(12) United States Patent
Kuo et al.

(10) Patent No.: US 11,216,942 B2
(45) Date of Patent: Jan. 4, 2022

(54) METHOD AND SYSTEM FOR DETECTING AND ANALYZING MUCOSA OF DIGESTIVE TRACT

(71) Applicant: National Yang-Ming University, Taipei (TW)

(72) Inventors: Wen-Chuan Kuo, Taipei (TW); Ping-Hsien Chen, New Taipei (TW); Chien-Hsien Wu, New Taipei (TW)

(73) Assignee: NATIONAL YANG-MING UNIVERSITY, Taipei (TW)

( * ) Notice: Subject to any disclaimer, the term of this patent is extended or adjusted under 35 U.S.C. 154(b) by 106 days.

(21) Appl. No.: 16/613,179

(22) PCT Filed: May 16, 2018

(86) PCT No.: PCT/US2018/032999
§ 371 (c)(1),
(2) Date: Nov. 13, 2019

(87) PCT Pub. No.: WO2018/213469
PCT Pub. Date: Nov. 22, 2018

(65) Prior Publication Data
US 2020/0184636 A1    Jun. 11, 2020

(30) Foreign Application Priority Data
May 16, 2017   (TW) .................................. 106116102

(51) Int. Cl.
*G06K 9/00*       (2006.01)
*G06T 7/00*       (2017.01)
(Continued)

(52) U.S. Cl.
CPC .............. *G06T 7/0012* (2013.01); *A61B 1/24* (2013.01); *A61B 1/2733* (2013.01);
(Continued)

(58) Field of Classification Search
CPC .................................................. G06T 7/0012
See application file for complete search history.

(56) References Cited

U.S. PATENT DOCUMENTS 6,514,082 B2   2/2003   Kaufman et al.
7,609,868 B2   10/2009  Kuth et al.
(Continued)

FOREIGN PATENT DOCUMENTS

CN    102355861 A    2/2012

*Primary Examiner* — Oneal R Mistry
(74) *Attorney, Agent, or Firm* — Muncy, Geissler, Olds & Lowe, P.C.

(57) ABSTRACT

A method and a system for detecting and analyzing a mucosa of a digestive tract are provided. The method includes detecting reply signals from the mucosa of the digestive tract within a depth range, acquiring 2D vascular images by performing a vascular enhancement on the reply signals, constructing a 3D vascular contrasting image of at least part of the mucosa of the digestive tract within the depth range by recombining at least part of the 2D vascular images, and reconstructing a 3D vascular contrasting projection image by performing a projection process to the 3D vascular contrasting image, and defining a stage of the mucosa of the digestive tract within the depth range according to the 3D
(Continued)

vascular contrasting projection image, the 3D vascular contrasting image, the 2D vascular images, and vessel morphologies shown therein.

17 Claims, 12 Drawing Sheets (51) Int. Cl.
*G06T 7/55* (2017.01)
*A61B 1/24* (2006.01)
*A61B 1/273* (2006.01)
*A61B 1/31* (2006.01)
*A61B 5/00* (2006.01)
*G06T 17/00* (2006.01)
*A61B 5/055* (2006.01)
*A61B 8/12* (2006.01)

(52) U.S. Cl.
CPC ............ *A61B 1/2736* (2013.01); *A61B 1/31* (2013.01); *A61B 5/489* (2013.01); *G06T 7/55* (2017.01); *G06T 17/00* (2013.01); *A61B 5/0066* (2013.01); *A61B 5/0068* (2013.01); *A61B 5/0084* (2013.01); *A61B 5/055* (2013.01); *A61B 8/12* (2013.01); *G06T 2207/10068* (2013.01); *G06T 2207/30028* (2013.01); *G06T 2207/30092* (2013.01); *G06T 2210/41* (2013.01)

(56) References Cited

U.S. PATENT DOCUMENTS

| | | | |
|---|---|---|---|
| 8,855,750 B2 | 10/2014 | Teramura | |
| 9,208,559 B1* | 12/2015 | Maschke | A61B 6/5235 |
| 2008/0058786 A1 | 3/2008 | Boyden et al. | |
| 2012/0150048 A1* | 6/2012 | Kang | G06T 7/149 |
| | | | 600/481 |
| 2013/0137926 A1* | 5/2013 | Itai | G06T 7/0012 |
| | | | 600/111 |
| 2015/0065868 A1 | 3/2015 | Liang et al. | |
| 2016/0381256 A1* | 12/2016 | Aguirre-Valencia | |
| | | | H04N 13/30 |
| | | | 348/46 |
| 2017/0000327 A1 | 1/2017 | Fingler et al. | |
| 2019/0056693 A1* | 2/2019 | Gelman | G02B 27/017 |

* cited by examiner

METHOD AND SYSTEM FOR DETECTING AND ANALYZING MUCOSA OF DIGESTIVE TRACT

CROSS-REFERENCE TO RELATED APPLICATION

The present disclosure is based on, and claims priority from Taiwan Application Serial Number 106116102, filed on May 16, 2017, the disclosure of which is hereby incorporated by reference herein in its entirety.

BACKGROUND OF INVENTION

1. Field of the Invention

The present invention generally relates to detection and analysis method and system, to be specific, to a method and system for detecting and analyzing a mucosa of a digestive tract.

2. Description of Related Art

The digestive tract is composed of mouth, throat, esophagus, stomach, and intestines. The squamous cell carcinoma which occurs in mouth, throat or esophagus is usually called oral cancer, throat cancer or esophagus cancer, that in stomach or intestines is usually called gastric cancer or intestinal cancer. Most cancers are transformed from the precancerous lesion; multiple pathological section samples are required to be taken from the region of the precancerous lesion to assist the doctor to make a correct pathological diagnosis. Before pathological slicing, some noninvasive methods can be used to find out appropriate positions for slicing, so as to reduce the number of slicing operations.

Doctors often use white light to irradiate mucosa, to observe the suspicious changes of the mucosa. However, it is difficult to visually find the difference between benign and malignant lesions. The staining is clinically used as assistance, but this method still has high false positive. In some case, the optical scanner is used to detecting tumor region of the digestive tract, the principle is to use blue light to irradiate the tissue, the normal mucosa presents green fluorescence for autofluorescence, and the tumor region presents black for lack of fluorescence. However, the benign inflammation region increases the blood supply in the lesion, the hemoglobin absorbs lots of light, resulting in the visible fluorescence disappearance the same as tumor region, so the recognition of dysplasia and benign inflammation lesion is still questioned.

In addition, a narrowband endoscope is an optical tool frequently used in recent years; it can be combined with a magnifying endoscope to observe squamous cell carcinoma of the esophagus, the sensitivity and specificity are higher than traditional white light. However, the limit of the image of narrowband endoscope only penetrates 240 μm, and the analysis of mucosa of mouth could be affected by ulcer and saliva. Moreover, the present techniques cannot quantify the observed mucosa condition.

The thickness variations and connection relationships of epithelium, basement membrane, and lamina propria are observed from the 2D image of the mucosa of the mouth. However, the single 2D image is difficult to provide distinct connection relationships among various layers, and it is difficult to define the thickness of various layers, so the difficulty level of pathological judgment of doctors will increase because of these problems.

Therefore, to overcome said defects and to enhance willingness for examination and to increase the probability of early detection of cancer are an urgent topic in current medicine.

SUMMARY OF THE INVENTION

The present invention provides a method for detecting and analyzing a mucosa of a digestive tract, comprising the following steps: detecting a plurality of reply signals from the mucosa of the digestive tract within a depth range; acquiring a plurality of 2D vascular images of the mucosa of the digestive tract within the depth range by performing a vascular enhancement on the plurality of reply signals; constructing a 3D vascular contrasting image of at least part of the mucosa of the digestive tract within the depth range by recombining at least part of the plurality of 2D vascular images; and reconstructing a 3D vascular contrasting projection image of the at least part of the mucosa of the digestive tract within the depth range by performing a projection process to the 3D vascular contrasting image, wherein at least one of the 3D vascular contrasting projection image, the 3D vascular contrasting image and the 2D vascular images shows a vessel morphology of the at least part of the mucosa of the digestive tract within the depth range.

In an embodiment, the method further includes defining a stage of the mucosa of the digestive tract within the depth range according to at least one of the 3D vascular contrasting image, the 3D vascular contrasting projection image, the vessel morphology.

In an embodiment, the method further includes obtaining a vessel morphological feature of the at least part of the mucosa of the digestive tract within the depth range by performing a quantitative analysis to the 3D vascular contrasting projection image, and defining the stage of the mucosa of the digestive tract within the depth range according to the vessel morphological feature. wherein the vessel morphological feature includes at least one of vessel area density, vessel diameter, and vessel bendiness.

Furthermore, the vessel morphology includes at least one of distribution, shape, bending, branching, merging, meandering, elongation, dilation, uniform, closed loop and opened loop.

In an embodiment, the method further includes obtaining the vessel morphological feature of the all of the mucosa of the digestive tract within the depth range by performing a quantitative analysis on the all 3D vascular contrasting projection image. wherein an all 3D vascular contrasting image of all of the mucosa of the digestive tract within the depth range is constructed by recombining all of the plurality of 2D vascular images, and an all 3D vascular contrasting projection image of all of the mucosa of the digestive tract within the depth range is reconstructed by performing the projection process to the all 3D vascular contrasting image.

In an embodiment, the method further includes segmenting the all 3D vascular contrasting image to form a part 3D vascular contrasting image, reconstructed a part 3D vascular contrasting projection image of the part of the mucosa of the digestive tract within the depth range by performing the projection process to the part 3D vascular contrasting image; and obtaining the vessel morphological feature of the part of the mucosa of the digestive tract within the depth range by performing a quantitative analysis on the part 3D vascular contrasting projection image.

In an embodiment, the method further includes obtaining the vessel morphological feature of the part of the mucosa of the digestive tract within the depth range by performing a quantitative analysis on the part 3D vascular contrasting projection image. wherein a part 3D vascular contrasting image of a part of the mucosa of the digestive tract within the depth range is constructed by recombining a part of the plurality of 2D vascular images, and a part 3D vascular contrasting projection image of the part of the mucosa of the digestive tract within the depth range is reconstructed by performing the projection process to the part 3D vascular contrasting image.

The mucosa of the digestive tract can be oral mucosa, esophageal mucosa, gastric mucosa and mucosa of intestines (e.g., duodenum, jejunum, ileum or large intestine). In an embodiment, the depth range is 0.001 to 3 mm. In an embodiment, the depth range is 0.001 to 6 mm. In an embodiment, the depth range is 0.001 to 15 mm.

The vascular enhancement includes phase or speckle-variance, correlation-mapping, split-spectrum amplitude-decorrelation, or optical microangiography.

In an embodiment, the method further includes transmitting a light to the mucosa of the digestive tract within the depth range, and receiving the reply signals from the mucosa of the digestive tract within the depth range, wherein the reply signals are a plurality of a combination coming from a reflected light of the mucosa at different depth within the depth range and a reference light.

The present invention further provides a system for detecting and analyzing a mucosa of a digestive tract, comprising a transmission apparatus transmitting a light into the mucosa of the digestive tract within a depth range; a probe connected to the transmission apparatus and receiving a reflected light from the mucosa of the digestive tract within the depth range; and a processor connected to the transmission apparatus.

The processor is configured to detect a plurality of reply signals from reflected light from the mucosa of the digestive tract within the depth range; acquire a plurality of 2D vascular images of the mucosa of the digestive tract within the depth range by performing a vascular enhancement on the plurality of reply signals; construct a 3D vascular contrasting image of at least part of the mucosa of the digestive tract within the depth range by recombining at least part of the plurality of 2D vascular images; and reconstruct a 3D vascular contrasting projection image of the at least part of the mucosa of the digestive tract within the depth range by performing a projection process to the 3D vascular contrasting image, wherein at least one of the 3D vascular contrasting projection image, the 3D vascular contrasting image, and the 2D vascular images shows a vessel morphology of the at least part of the mucosa of the digestive tract within the depth range.

BRIEF DESCRIPTION OF THE DRAWINGS

FIGS. 3A-1 to 3A-3, 3B-1 to 3B-3, 3C-1 to 3C-3 and 3D-1 to 3D-3 show 3D vascular contrasting projection images of the mucosa of the digestive tract within a depth range, which show all mucosa within the depth range, a superficial mucosal layer within the depth range and a deep mucosal layer within the depth range in examples 1 to 4 respectively;

DETAILED DESCRIPTION OF THE INVENTION

The embodiment of the present invention described above is to be regarded in all respects as being illustrative and nonrestrictive. Accordingly, the present invention may be embodied in other specific forms without deviating from the spirit thereof. The present invention is, therefore, to be limited only by the scopes of the following claims.

Figure 1:
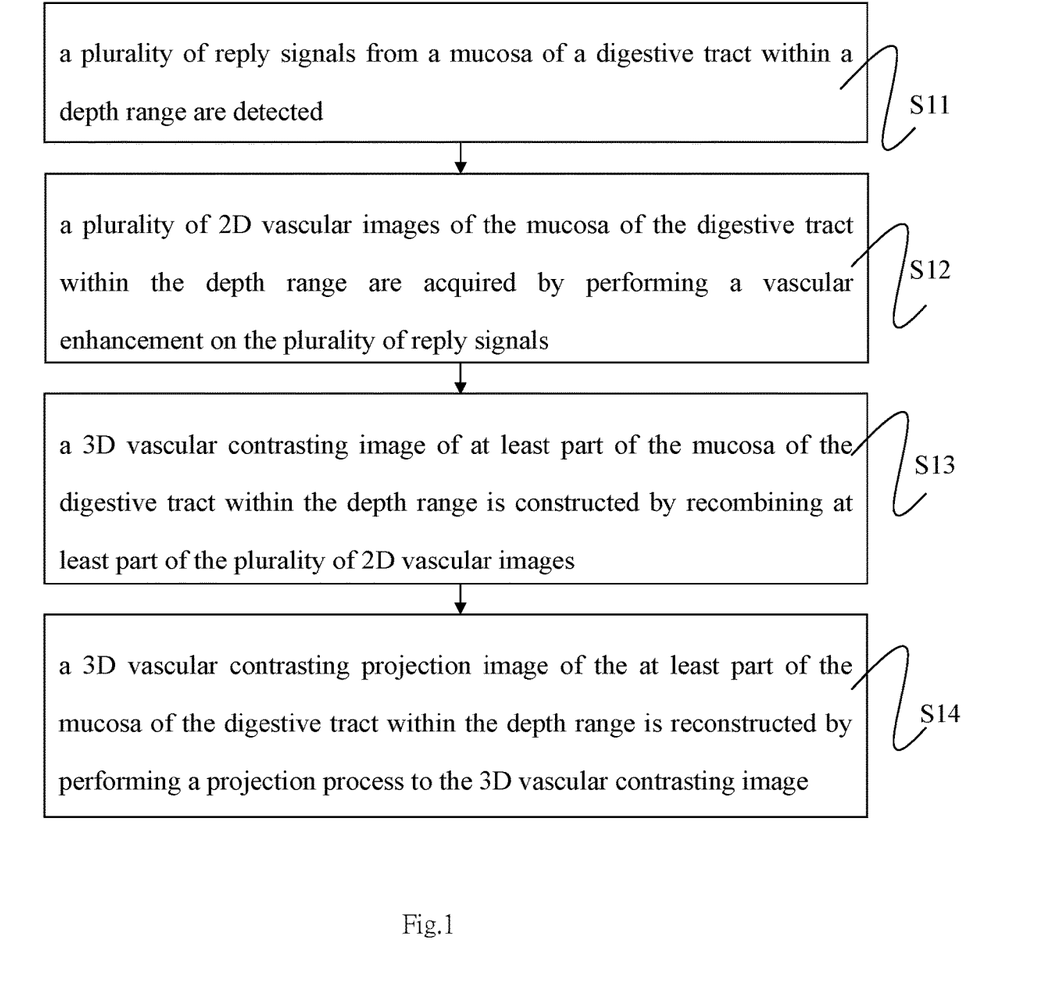
FIG. 1 is a schematic flow chart illustrating a method for detecting and analyzing a mucosa of a digestive tract according to the present invention.

FIG. 1 shows a schematic flow chart of a method for detecting and analyzing a mucosa of a digestive tract according to the present invention.

As shown in Step S11, a plurality of reply signals from a mucosa of a digestive tract within a depth range are detected. For example, the depth range is, e.g., 0.001 to 6 mm, 0.001 to 3 mm or 0.001 to 15 mm below the mucosa surface. The mucosa of the digestive tract can be oral mucosa, the mucosa of esophagus or gastrointestinal tract.

In addition, in this step, a light can be transmitted into the mucosa of the digestive tract to a depth range, and then a reflected light from the mucosa of the digestive tract within the depth range can be received, such that the reflected light and a reference light can form spectral interferograms to serve as the reply signals. For example, the optical coherence tomography (OCT) technique or other techniques which can transmit the light to reach the depth range can be used, e.g. MRI, ultrasonic imaging or confocal microscopy. The OCT technique includes time-domain OCT, frequency-domain OCT or frequency swept light source OCT technique.

In an embodiment, a transmission apparatus can be used to transmit the light, a probe connected with the transmission apparatus can be used to receive the reflected light, and a processor connected with the transmission apparatus can be used to detect the reply signals from the reflected light and the reference light.

The oral mucosa within about 3 mm below the mucosa surface includes epithelial layer (EP), basement membrane, and lamina propria (LP), so the reply signals from these tissues can be detected.

As shown in Step S12, a plurality of 2D vascular images of the mucosa of the digestive tract within the depth range are acquired by performing a vascular enhancement on the plurality of reply signals. In an embodiment, the vascular enhancement is a vascular algorithm, such as phase or speckle-variance, correlation-mapping, split-spectrum amplitude-decorrelation, or optical microangiography, performed by the processor.

Moreover, in an embodiment, the Z-axis represents the depth direction of the mucosa of the digestive tract, the 2D vascular images of Z-X (or Z-Y) section or X-Y section of the mucosa of digestive tract can be acquired, depending on which part of mucosa the reply signal comes from.

As shown in Step S13, a 3D vascular contrasting image of at least part of the mucosa of the digestive tract within the depth range is constructed by recombining at least part of the plurality of 2D vascular images. In an embodiment, the plurality of 2D vascular images of Z-X (or Z-Y) section or X-Y section obtained in Step S12 are recombined, so as to obtain the 3D vascular contrasting image of X-Y-Z.

As shown in Step S14, a 3D vascular contrasting projection image of the at least part of the mucosa of the digestive tract within the depth range is reconstructed by performing a projection process to the 3D vascular contrasting image. In an embodiment, the 3D vascular contrasting projection image is reconstructed by projecting the 3D vascular contrasting image on a plane in a choosing coordinate reference.

Moreover, at least one of the 3D vascular contrasting projection image, the 3D vascular contrasting image, and the 2D vascular images shows a vessel morphology, such as distribution, shape, bending, branching, merging, meandering, elongation, dilation, uniform, closed loop and opened loop, as shown in FIGS. 3A-1 to 3D-3, 4A, 5A, and 6A.

Furthermore, a vessel morphological feature, such as vessel area density, vessel median diameter, and vessel bendiness, can be obtained by performing a quantitative analysis to the 3D vascular contrasting projection image, as shown in FIGS. 4B-4D, 5B-5D and 6B-6D.

From the foregoing, as the reply signals in Step 11 come from all of the mucosa of the digestive tract within the depth range and the 2D vascular images in Step 12 show vessels of all of the mucosa of the digestive tract within the depth range, during the recombination in Step S13, the 3D vascular contrasting image of all (whole layer) or part (one layer) of the mucosa of the digestive tract within the depth range can be constructed optionally, which is to say, the range, prision, angle to be projected of the mucosa within the depth can be determined as required, so that the vessel morphology of different layers of the mucosa within the depth range can be analyzed in subsequent quantitative analysis.

Thereby, the stages of the mucosa of the digestive tract within the depth range can be defined according to the 3D vascular contrasting image, 3D vascular contrasting projection image vessel morphology or vessel morphological feature.

Figure 4A:
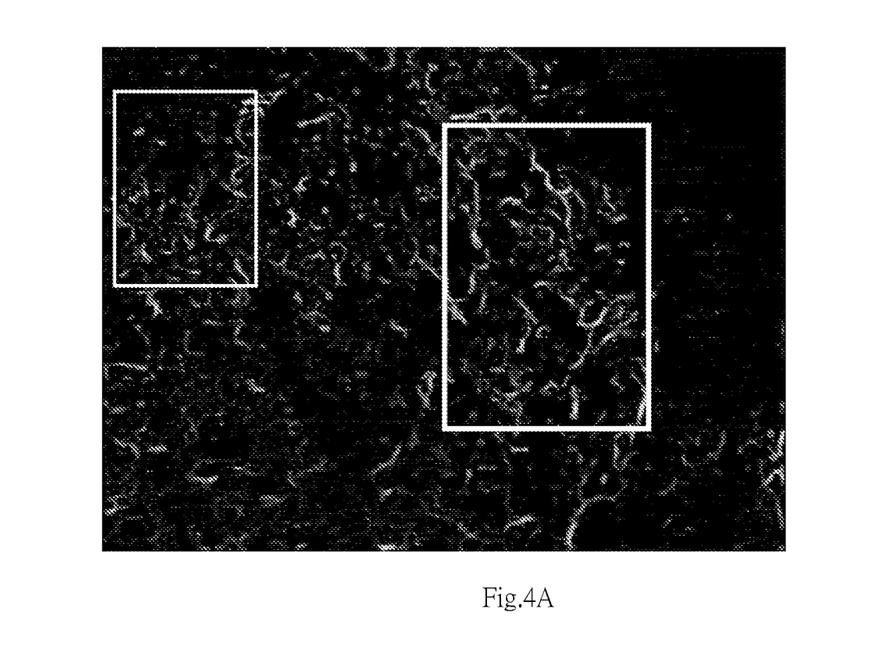
FIGS. 4A to 4D show a 3D vascular contrasting projection image, a vessel area density quantization, a vessel median diameter quantization and a vessel bendiness quantization of all mucosa of the digestive tract within a depth range in example 5, respectively.

In an embodiment, an all 3D vascular contrasting image of all of the mucosa within the depth range is constructed by recombining all of the 2D vascular images, and an all 3D vascular contrasting projection image of the all of the mucosa within the depth range is reconstructed by performing the projection process to the all 3D vascular contrasting image. In addition, the all 3D vascular contrasting image and the all 3D vascular contrasting projection image each presents vessel morphology, such as distribution, shape, bending, branching, merging, meandering, elongation, dilation, uniform, closed loop and opened loop, as shown in FIG. 4A.

Figure 4B:
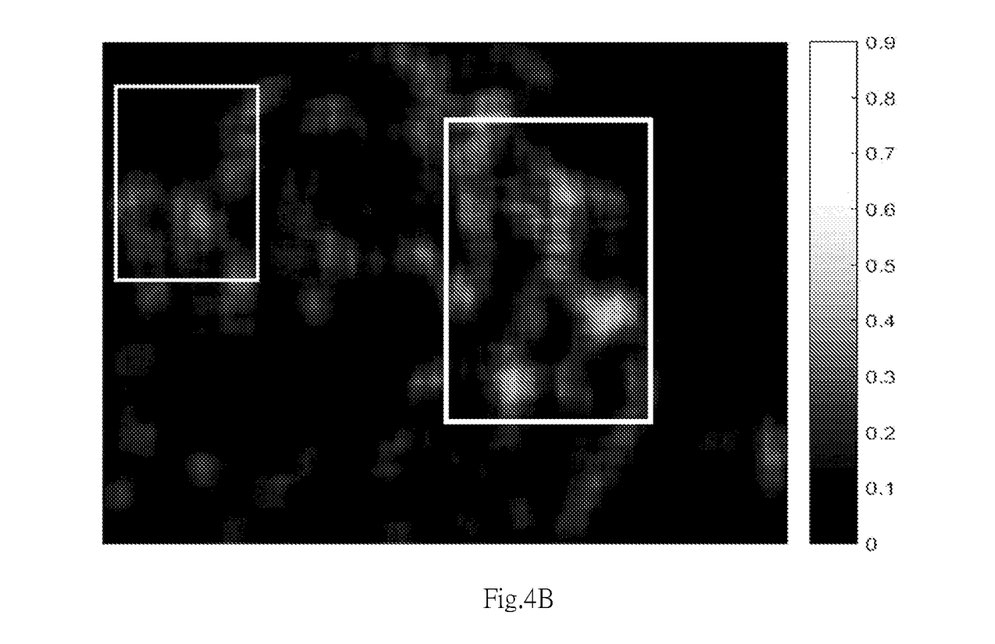
Figure 4C:
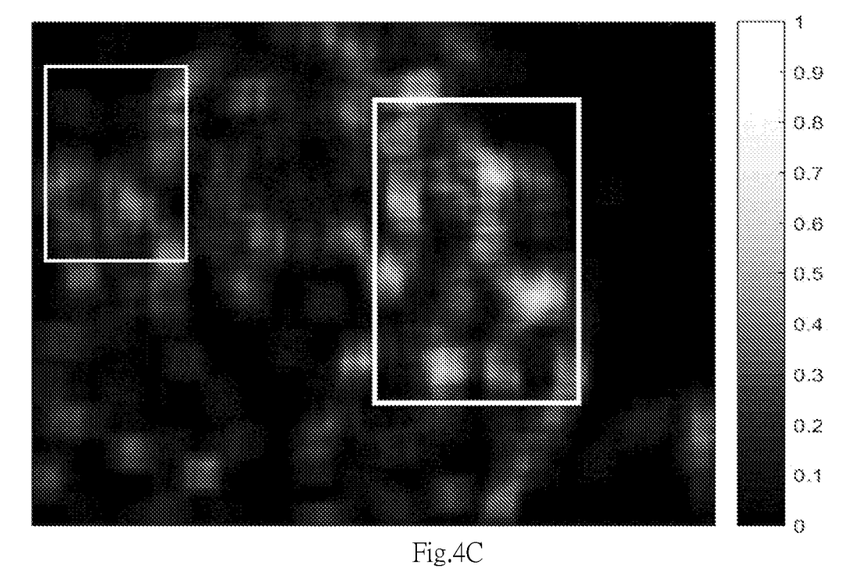
Figure 4D:
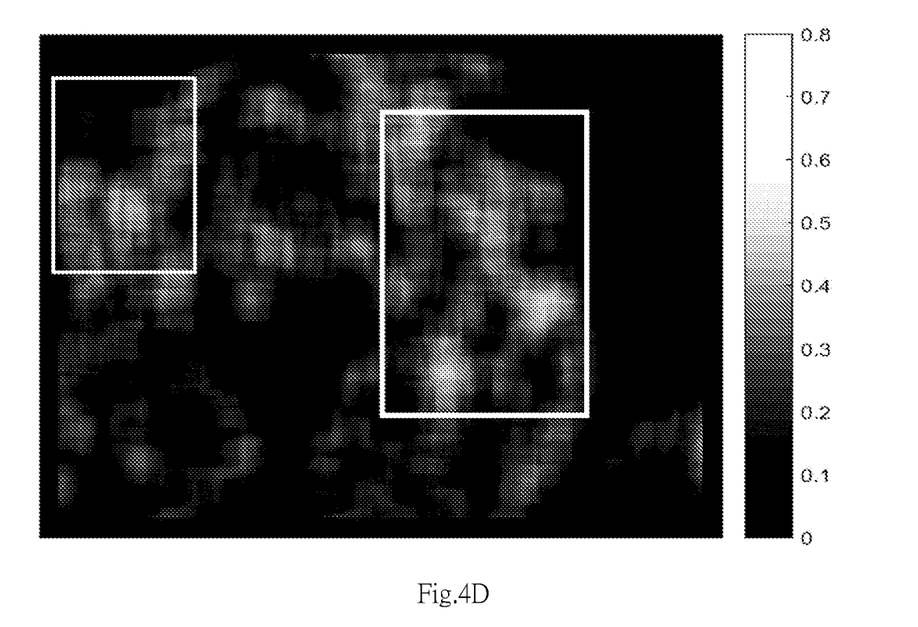

Moreover, a quantitative analysis can be performed on the all 3D vascular contrasting projection image of all of the mucosa within the depth range to obtain the vessel morphological feature of all of the tissue within the depth of the mucosa of the digestive tract, e.g. a quantitative vessel area density, a quantitative vessel median diameter or a quantitative vessel bendiness, as shown in FIGS. 4B to 4D.

In another embodiment, an all 3D vascular contrasting image of all of the mucosa within the depth rang is constructed by recombining all of the 2D vascular images, the all 3D vascular contrasting image can be segmented to obtain a part 3D vascular contrasting image, and the projection process is performed to the part 3D vascular contrasting image so as to obtain a part 3D vascular contrasting projection image of the part of the mucosa within the depth range.

Figure 5A:
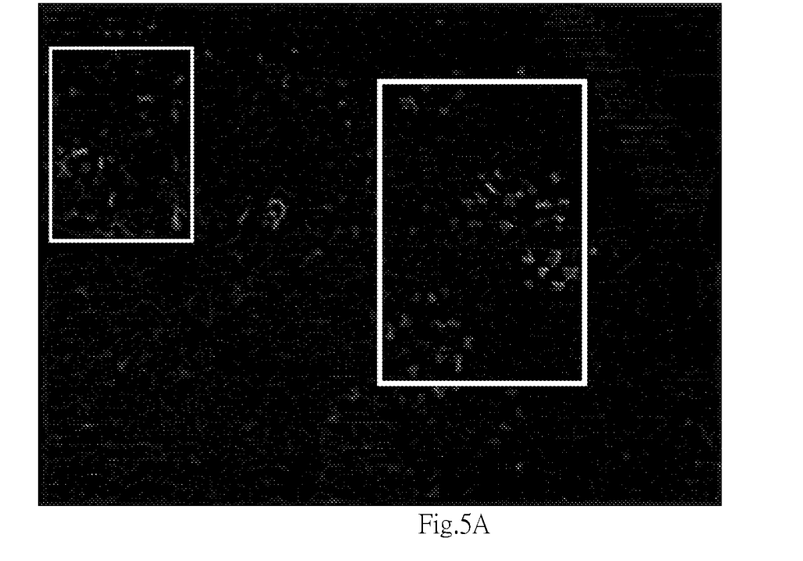
FIGS. 5A to 5D show a 3D vascular contrasting projection image, a quantitative vessel area density quantization, a vessel median diameter quantization and a vessel bendiness quantization of a superficial mucosal layer of the digestive tract within the depth range in example 5, respectively.
Figure 5B:
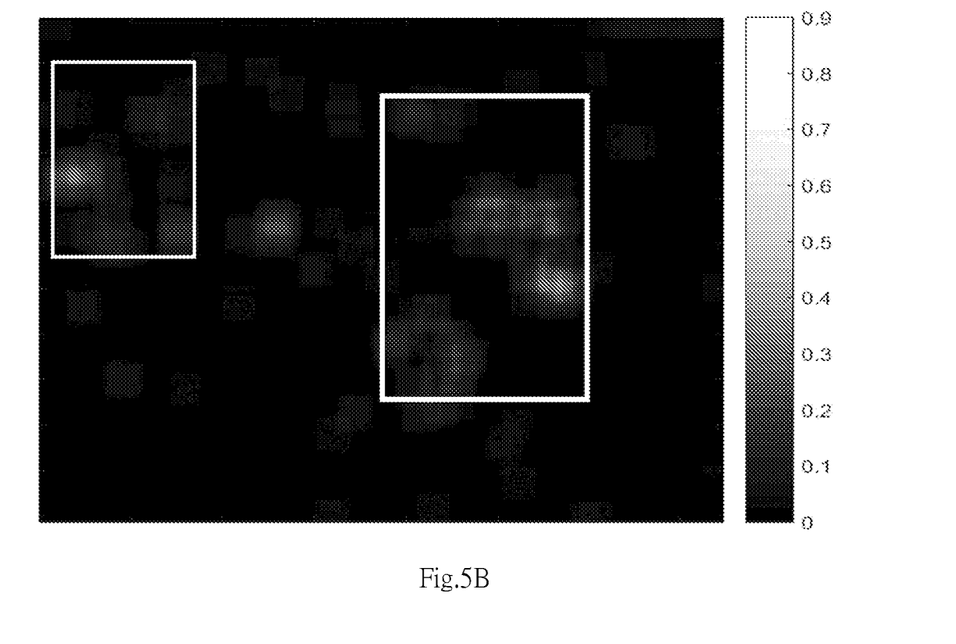
Figure 5C:
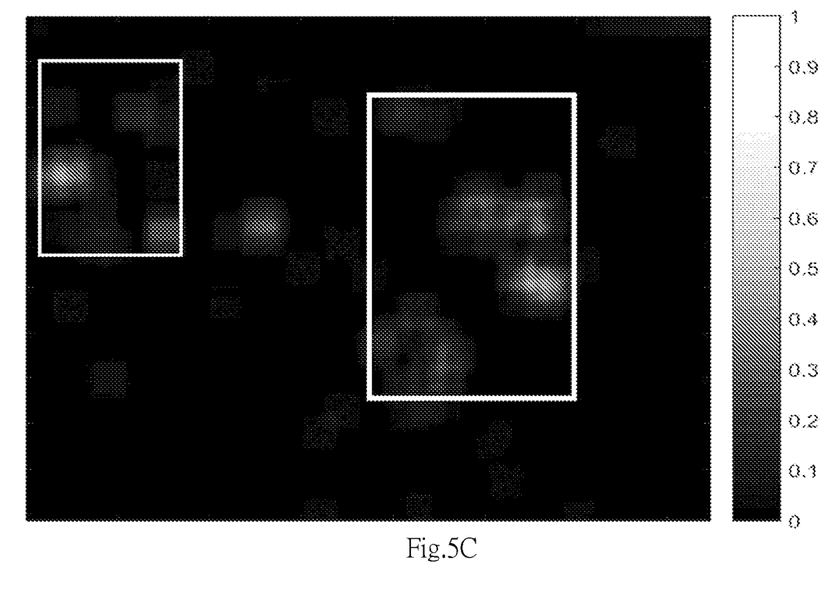
Figure 5D:
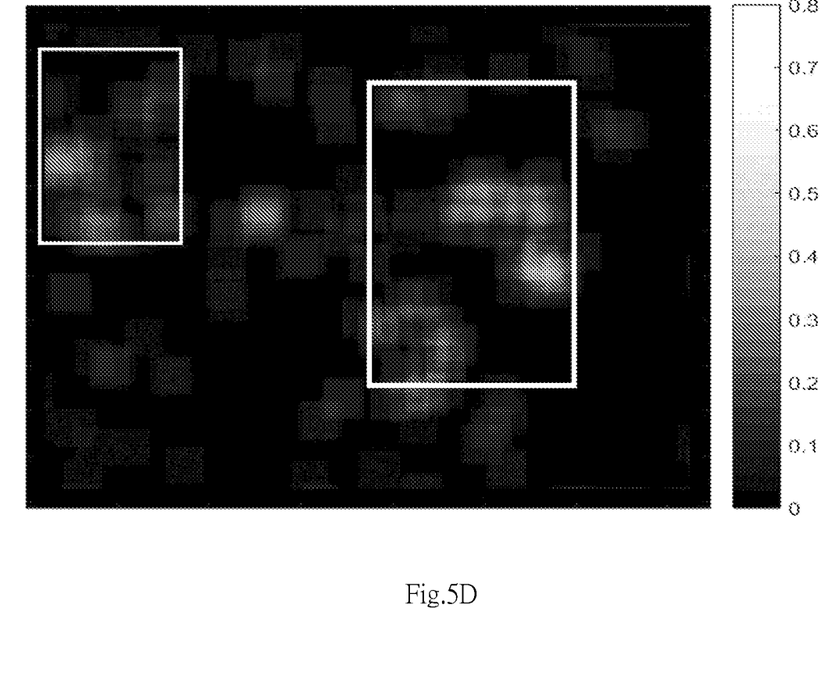
Figure 6A:
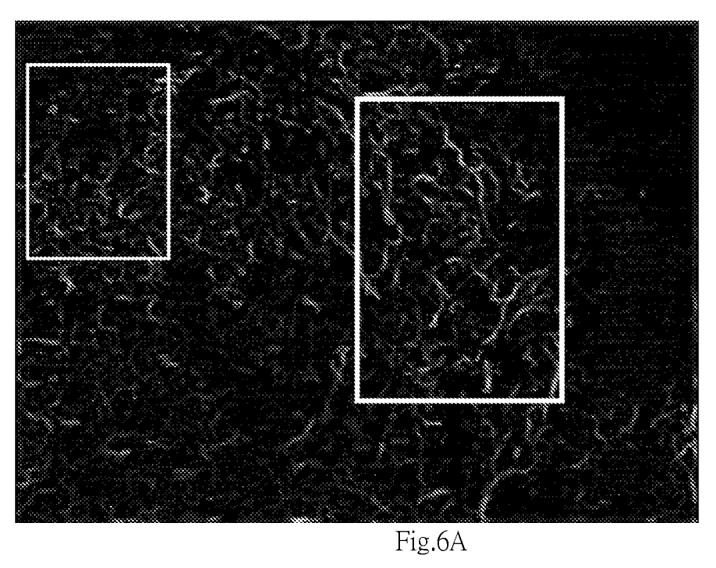
FIGS. 6A to 6D show a 3D vascular contrasting projection image, a vessel area density quantization, a vessel median diameter quantization, and a vessel bendiness quantization of a deep mucosal layer of the digestive tract within the depth range in example 5, respectively.

In yet another embodiment, a part 3D vascular contrasting image of a part of the mucosa within the depth range is constructed by recombining a part of the 2D vascular images, and the projection process is performed to the part 3D vascular contrasting image so as to obtain a part 3D vascular contrasting projection image of the part of the mucosa within the depth range. The part 3D vascular contrasting projection image represents the vessel morphology, such as distribution, shape, bending, branching, merging, meandering, elongation, dilation, uniform, closed loop and opened loop, of the EP or LP, as shown in FIGS. 5A and 6A. Afterwards, the vessel morphological feature analysis is performed on the part 3D vascular contrasting projection image so as to obtain the vessel morphological feature of the layer of the tissue within the depth of the mucosa of the digestive tract, as shown in FIGS. 5B to 5D or FIGS. 6B to 6D.

Figure 2:
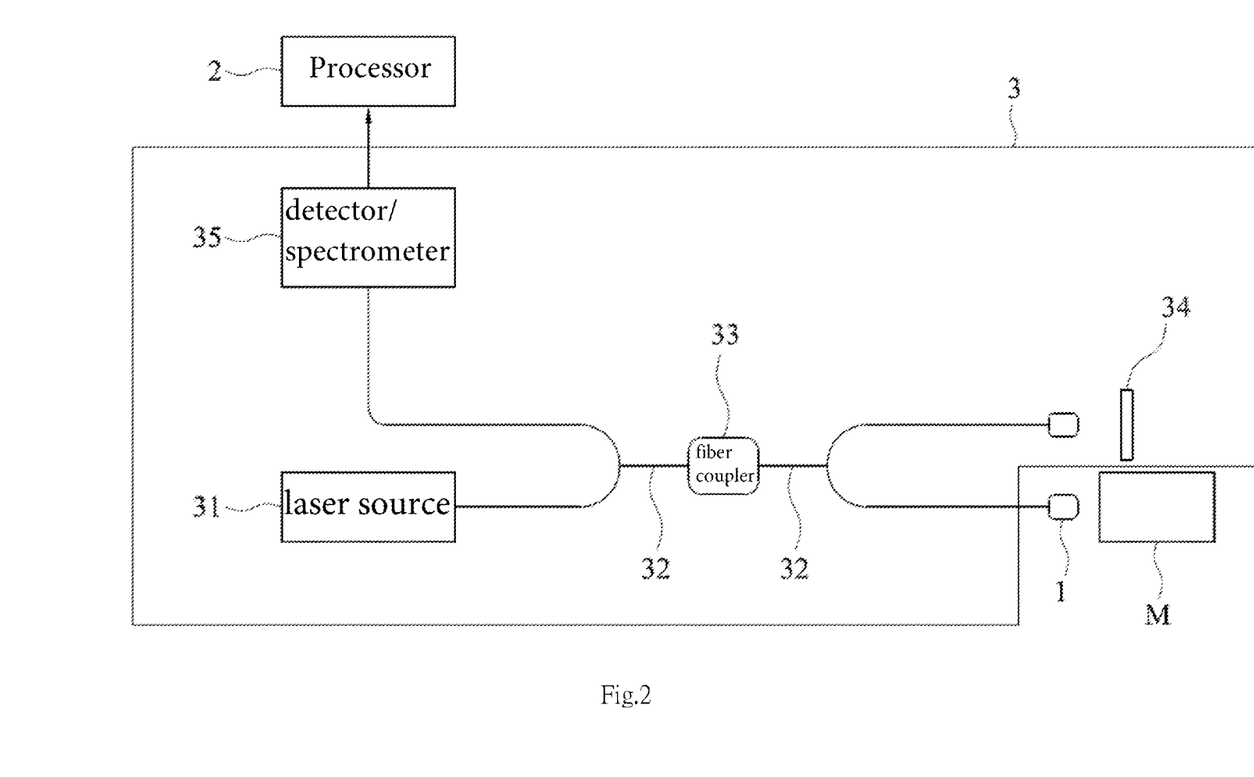
FIG. 2 is a schematic diagram illustrating a system for detecting and analyzing a mucosa of a digestive tract according to the present invention.

Referring to FIG. 2, a system for detecting and analyzing the mucosa of the digestive tract according to the present invention is illustrated. As shown in FIG. 2, the system comprises a transmission apparatus 3, a probe 1 connected to transmission apparatus 3 and a processor 2 communicating with the transmission apparatus 3.

The transmission apparatus 3, e.g., OCT equipment, comprises a laser source 31, an optical fiber 32, a fiber coupler 33, an optical mirror 34 and a detector/spectrometer 35. The OCT equipment has simple light path calibration and processing requirements and can scan the mucosa quickly for the processor 2 to perform a processing operation. The OCT equipment can comprise other components of similar quantity or function.

The probe 1 is provided for the OCT equipment to perform OCT on the mucosa of digestive tract M within the depth range (e.g., 0.001 to 3 mm, 0.001 to 6 mm or 0.001 to 15 mm below mucosa) through probe 1. In an embodiment, the mucosa of digestive tract M is oral mucosa, the probe 1 can be designed as a structure which can be put in the oral cavity to receive the reply signals from the oral cavity. In an embodiment, the laser source 31 is frequency swept light source, the detector/spectrometer 35 is a detector, and, for example, the laser source 31 is the broadband light source, the detector/spectrometer 35 is a spectrometer.

In an embodiment, a light is transmitted by the transmission apparatus 3 through the probe 1 to the mucosa of the digestive tract M within the depth range, and a reflected light from the mucosa of the digestive tract M within the depth range is received by the transmission apparatus 3 through the probe 1. The reflected light and a reference light can form spectral interferograms, which serves as the reply signals, for the processor 2 to detect it.

The processor 2 can be connected to an analog-digital converter and a database (not shown) connected to the transmission apparatus 3, and can detect the reply signals from the mucosa of the digestive tract M within the depth range, acquire 2D vascular images of the mucosa of the digestive tract M within the depth range by performing the vascular enhancement on the reply signals, construct a 3D vascular contrasting image of at least part of the mucosa of the digestive tract M within the depth range by recombining at least part of the 2D vascular images, and reconstruct a 3D vascular contrasting projection image of the at least part of the mucosa of the digestive tract M within the depth range by performing a projection process to the 3D vascular contrasting image. Afterwards, the quantitative analysis can be performed on the 3D vascular contrasting projection image, so as to obtain the vessel morphological feature, e.g. vessel area density, vessel median diameter or vessel bendiness.

In an embodiment, the vascular enhancement includes phase or speckle-variance, correlation-mapping, split-spectrum amplitude-decorrelation, or optical microangiography. The 2D vascular images, the 3D vascular contrasting image, and the 3D vascular contrasting projection image each can represent a vessel morphology, such as distribution, shape, bending, branching, merging, meandering, elongation, dilation, uniform, closed loop and opened loop, as shown in FIGS. 3A-1 to 3D-3, 4A, 5A and 6A.

As such, according to the vessel morphological feature, vessel morphology, 3D vascular contrasting projection image, or 3D vascular contrasting image of the mucosa of the digestive tract within the depth range, the pathological stages of disease progression of the mucosa can be find.

Referring to FIGS. 3A-1 to 3A-3, 3B-1 to 3B-3, 3C-1 to 3C-3 and 3D-1 to 3D-3, the experimental results of examples 1 to 4 are provided. It shall be noted that the experimental subjects of examples 1 to 4 are oral mucosa of living body #1, #2, #3 and #4, and it is unnecessary to separate the oral mucosa from the living body for slicing. The steps according to FIG. 2 can be performed for oral mucosa of living body #1, #2, #3 and #4 to obtain the experimental results.

EXAMPLE 1

Figure 3A:
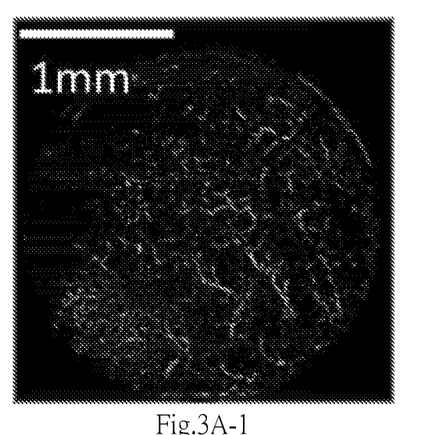
Figure 3A:
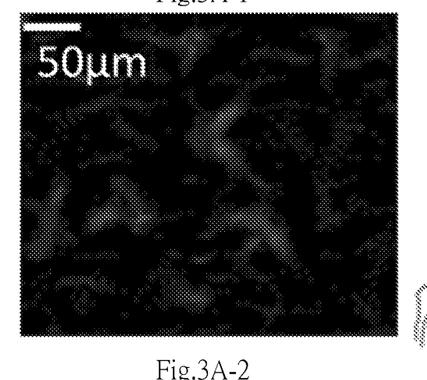
Figure 3A:
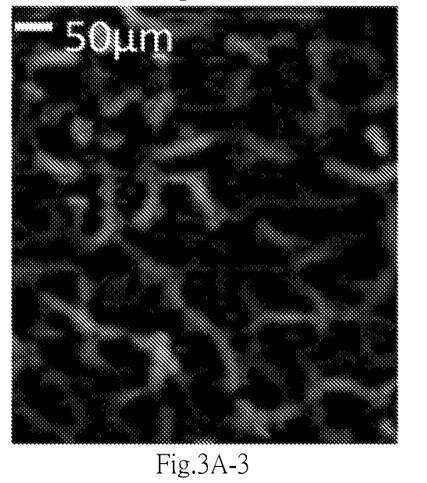

FIG. 3A-1 shows a 3D vascular contrasting projection image of the oral mucosa within the depth range of living body #1 in normal histology. FIG. 3A-2 shows a 3D vascular contrasting projection image of a superficial mucosal layer (e.g., EP) of the oral mucosa of living body #1 in normal histology, with a vessel morphology schematically shown at lower right corner. FIG. 3A-3 shows a 3D vascular contrasting projection image of a deep mucosal layer (e.g., LP) of the oral mucosa of living body #1 in normal histology.

EXAMPLE 2

Figure 3B:
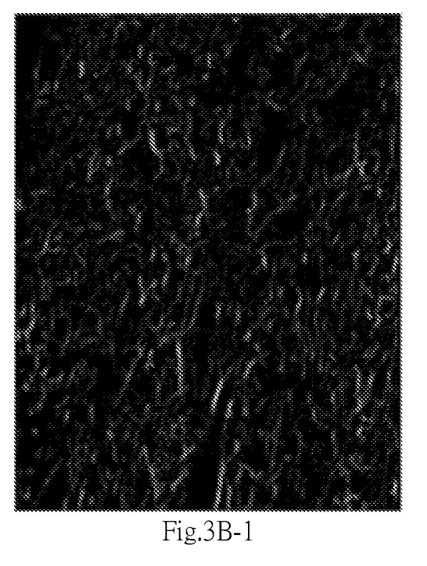
Figure 3B:
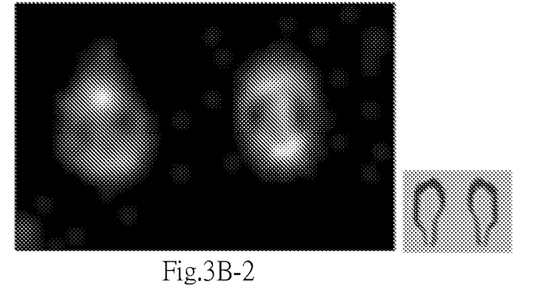
Figure 3B:
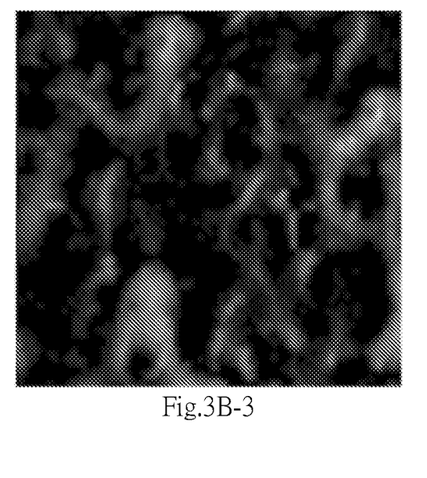

FIG. 3B-1 shows a 3D vascular contrasting projection image of the oral mucosa within the depth range of living body #2 in high-grade dysplasia (HGD). FIG. 3B-2 shows a 3D vascular contrasting projection image of a superficial mucosal layer (e.g., EP) of the oral mucosa of living body #2 in HGD, with a vessel morphology is schematically shown at lower right corner. FIG. 3B-3 shows a 3D vascular contrasting projection image of a deep mucosal layer (e.g., LP) of the oral mucosa of living body #2 in HGD.

EXAMPLE 3

Figure 3C:
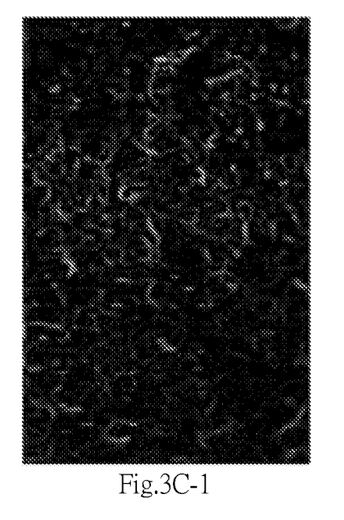
Figure 3C:
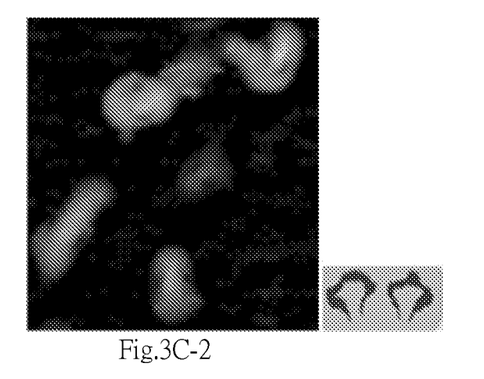
Figure 3C:
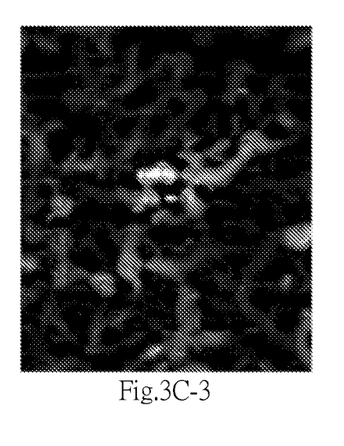

FIG. 3C-1 shows a 3D vascular contrasting projection image of the oral mucosa within the depth range of living body #3 in carcinoma in situ (CIS). FIG. 3C-2 shows a 3D vascular contrasting projection image of a superficial mucosal layer (e.g., EP) of the oral mucosa of living body #3 in CIS, with a vessel morphology is schematically shown at lower right corner. FIG. 3C-3 shows a 3D vascular contrasting projection image of a deep mucosal layer (e.g., LP) of the oral mucosa of living body #3 in CIS.

EXAMPLE 4

Figure 3D:
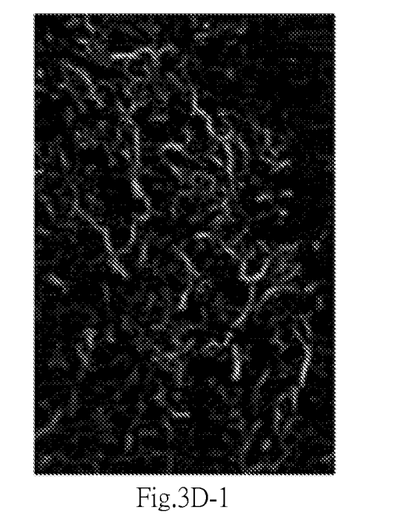
Figure 3D:
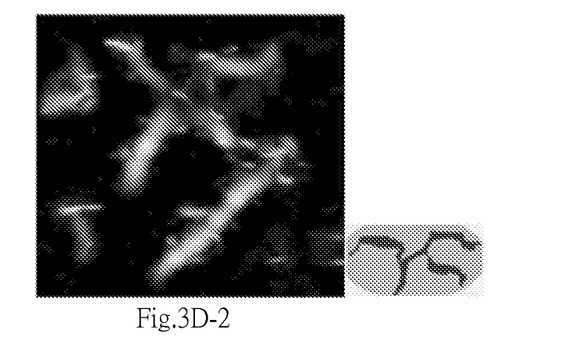
Figure 3D:
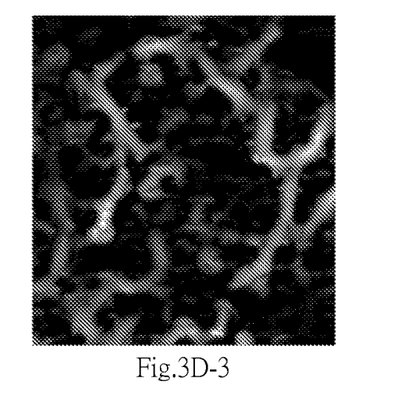

FIG. 3D-1 shows a 3D vascular contrasting projection image of the oral mucosa within the depth range of living body #4 in advanced squamous cell carcinoma (SCC). FIG. 3D-2 shows a 3D vascular contrasting projection image of a superficial mucosal layer (e.g., EP) of the oral mucosa of living body #4 in advanced SCC, with a vessel morphology schematically shown at lower right corner. FIG. 3D-3 shows a 3D vascular contrasting projection image of a deep mucosal layer (e.g., LP) of the oral mucosa of living body #4 in advanced SCC.

FIGS. 3A-1 to 3A-3, 3B-1 to 3B-3, 3C-1 to 3C-3 and 3D-1 to 3D-3 show the variations in vasculature from normal, HGD, CIS, to advanced SCC. Therefore, the variations of vasculature in different pathological stages of disease progression can be distinguished more accurately by the 3D vascular contrasting image or vascular contrasting projection image of tissues in different depths of mucosa, e.g., benign precancerous lesion and malignant tumor. In addition, there are such advantages as noninvasiveness, fast and wide scan, and any layered image can be recombined or segmented for multiangular observation, further vascular variation can be obtained, so as to define the pathological stages of the oral mucosa.

It can be seen from the 3D vascular contrasting projection images of different layers of the oral mucosa that the vessel morphology of the superficial mucosal layer and the deep mucosal layer change as the disease occurs. For example, the vessel morphology of EP in normal is a non-dilating loop, as shown in FIG. 3A-2; the vessel morphology of EP in HGD is a lightly dilating loop, as shown in FIG. 3B-2; the vessel morphology of EP in CIS is an dilating, opened loop, as shown in FIG. 3C-2, and the vessel diameter is increasing; and the vessel morphology of EP in advanced SCC has turned into irregular branches, as shown in FIG. 3D-2. The vessel morphology of LP has changed in density and caliber. Therefore, according to FIGS. 3A-3 to 3D-3, the vessels merge and dilation with tumor formation, and the density and branch bendiness increase.

EXAMPLE 5

The vessel morphological feature of the mucosa within a depth range of oral mucosa of living body #5 is described in example 5. A quantitative analysis can be performed on the 3D vascular contrasting projection images to obtain the vessel morphological feature for providing more references.

Referring to FIGS. 4A to 4D, a 3D vascular contrasting projection image, a quantitative vessel area density, a quantitative vessel median diameter, and a quantitative vessel bendiness of the mucosa within a depth range of oral mucosa of living body #5 are provided.

FIG. 4A shows a 3D vascular contrasting projection image of the mucosa within a depth range of oral mucosa of living body #5. This image shows CIS (left rectangle) and advanced SCC (right rectangle). In the vessel area density quantization of FIG. 4B, different gray levels from dark to bright represent different vessel area densities. The brighter the gray level is, the higher is the vessel area density. More bright blocks represent more high-density regions. For example, the region of the right rectangle (advanced SCC) has higher vessel area density than the region of the left rectangle (CIS). In the vessel median diameter quantization of FIG. 4C, different vessel median diameters are distinguished by different gray levels. The brighter the gray level is, the larger is the caliber, and more bright blocks represent more large caliber regions. For example, the region of the right rectangle (advanced cancer) has larger vessel median diameter than the region of the left rectangle (carcinoma in situ). In the vessel bendiness quantization of FIG. 4D, different vessel bendiness are distinguished by different gray levels. The brighter the gray level is, the larger is the bendiness, and more bright blocks represent more large bendiness regions. For example, the region of the right rectangle (advanced cancer) has larger vessel bendiness than the region of the left rectangle (carcinoma in situ).

EXAMPLE 6

The vessel morphological feature of mucosa of different layers within a depth of oral mucosa of living body #5 are described by example 6.

Referring to FIGS. 5A to 5D, a 3D vascular contrasting projection image, a vessel area density quantization, a vessel median diameter quantization and a vessel bendiness quantization of the superficial mucosal layer of oral mucosa of living body #5 respectively are provided. In addition, FIGS. 6A to 6D show a 3D vascular contrasting projection image, a quantization of vessel area density, a quantization of vessel median diameter, and a quantization of vessel bendiness of a deep mucosal layer of oral mucosa of living body #5 respectively.

FIG. 5A shows a 3D vascular contrasting projection image of the superficial mucosal layer of oral mucosa of living body #5. This image shows CIS (left rectangle) and advanced SCC (right rectangle). In the vessel area density quantization of FIG. 5B, the brighter the gray level is, the higher is the vessel area density and more bright blocks represent more high vessel area density regions. For example, the vessel area density in the region of right rectangle is higher than the vessel area density in the region of the left rectangle. In the vessel median diameter quantization of FIG. 5C, the brighter the gray level is, the larger is the caliber, and more bright blocks represent more large caliber regions. For example, the vessel median diameter in the region of the right rectangle (advanced cancer) is larger than the vessel median diameter in the region of the left rectangle (CIS). In the vessel bendiness quantization of FIG. 5D, the brighter the gray level is, the larger is the bendiness, and more bright blocks represent more large bendiness regions. FIGS. 5B to 5D show the vessel morphological feature of the EP of oral mucosa of living body #5 in Embodiment 6.

Figure 6B:
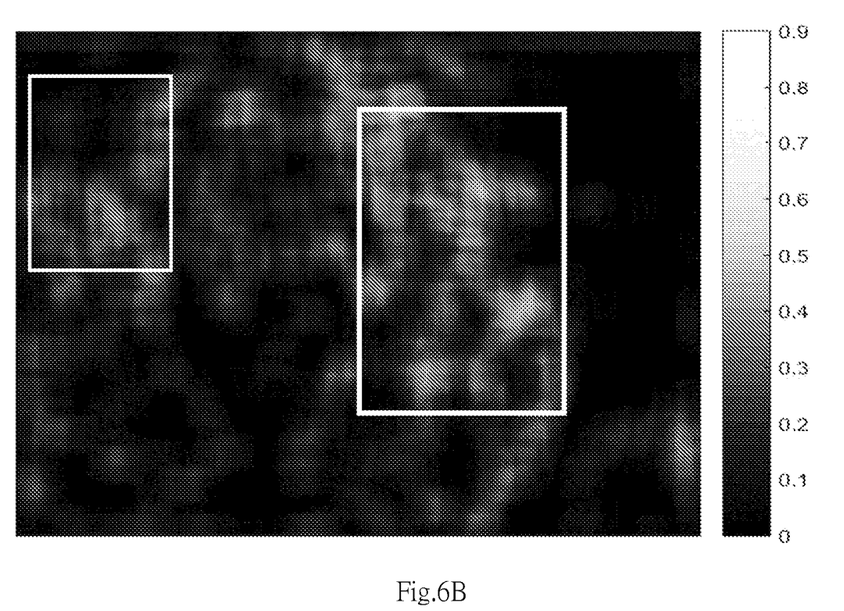
Figure 6C:
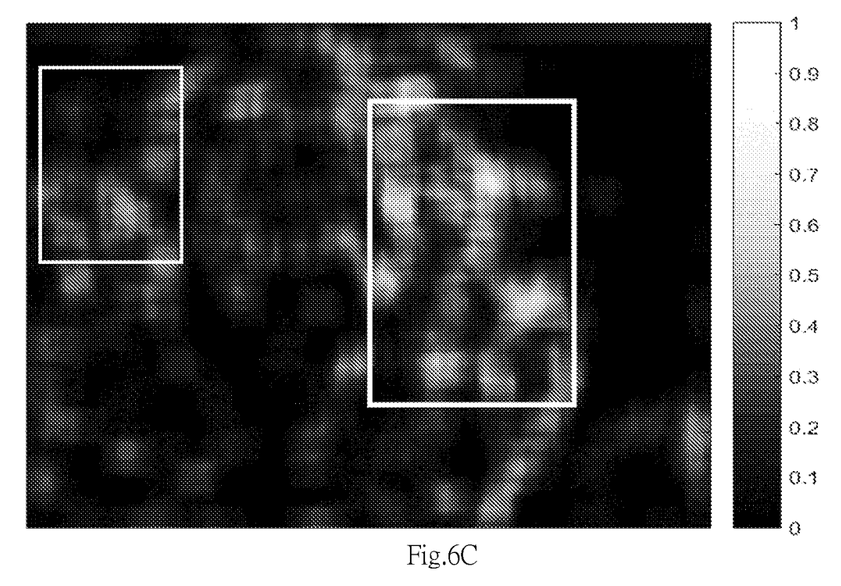
Figure 6D:
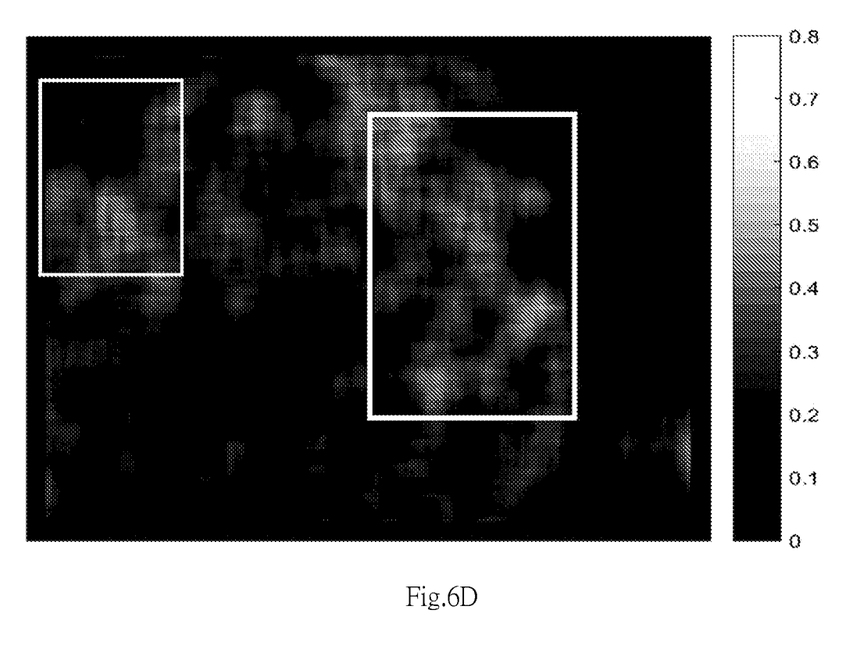

FIG. 6A shows a 3D vascular contrasting projection image of a deep mucosal layer of oral mucosa of living body #5. This image shows CIS (left rectangle) and advanced SCC (right rectangle). In the vessel area density quantization of FIG. 6B, more bright blocks represent more high-density regions. For example, the vessel area density in the region of the right rectangle (advanced SCC) is higher than the vessel area density in the region of the left rectangle (carcinoma in situ). In the vessel median diameter quantization of FIG. 6C, the brighter the gray level is, the larger is the caliber, and more bright blocks represent more large caliber regions. For example, the vessel median diameter in the region of the right rectangle (advanced SCC) is larger than the vessel median diameter in the region of the left rectangle (carcinoma in situ). In the vessel bendiness quantization of FIG. 6D, the brighter the gray level is, the larger is the bendiness, and more bright blocks represent more large bendiness regions. FIGS. 6B to 6D show the vessel morphological feature of lamina propria of oral mucosa of living body #6 in Embodiment 6.

As above, the present invention can perform real-time angiography on a living body without pathological section. According to the present invention, the vessel morphology, such as distribution, shape, bending, branching, merging, meandering, elongation, dilation, uniform, closed loop and opened loop, and the vessel morphological feature, such as vessel area density, vessel diameter and vessel bendiness in different depth ranges of the mucosa of the digestive tract can be obtained, such that the change in vasculature in different pathological processes can be defined, thereby assisting in determining the pathological stages of mucosa and identifying the benignancy and malignancy of disease.

Although the present invention has been described in terms of specific exemplary embodiments and examples, it will be appreciated that the embodiments disclosed herein are for illustrative purposes only, and various modifications and alterations might be made by those skilled in the art without departing from the spirit and scope of the invention as set forth in the following claims.

What is claimed is:

1. A method for detecting and analyzing a mucosa of a digestive tract, the method comprising:
   detecting a plurality of reply signals from the mucosa of the digestive tract within a depth range;
   acquiring a plurality of 2D vascular images of the mucosa of the digestive tract within the depth range by performing a vascular enhancement on the plurality of reply signals;
   constructing a 3D vascular contrasting image of at least part of the mucosa of the digestive tract within the depth range by recombining at least part of the plurality of 2D vascular images; and reconstructing a 3D vascular contrasting projection image of the at least part of the mucosa of the digestive tract within the depth range by performing a projection process to the 3D vascular contrasting image;
   wherein at least one of the 3D vascular contrasting projection image, the 3D vascular contrasting image, and the 2D vascular images shows a vessel morphology of the at least part of the mucosa of the digestive tract within the depth range,
   wherein an all 3D vascular contrasting image of all of the mucosa of the digestive tract within the depth range is constructed by recombining all of the plurality of 2D vascular images,
   wherein the method further comprises:
   segmenting the all 3D vascular contrasting image to form a part 3D vascular contrasting image;
   reconstructing a part 3D vascular contrasting projection image of the part of the mucosa of the digestive tract within the depth range by performing the projection process to the part 3D vascular contrasting image; and
   obtaining a vessel morphological feature of the part of the mucosa of the digestive tract within the depth range by performing a quantitative analysis on the part 3D vascular contrasting projection image.

2. The method defined in claim 1, further comprising:
   defining a stage of the mucosa of the digestive tract within the depth range according to at least one of the 3D vascular contrasting image, the 3D vascular contrasting projection image and the vessel morphology.

3. The method defined in claim 1, further comprising:
   obtaining a vessel morphological feature of the at least part of the mucosa of the digestive tract within the depth range by performing a quantitative analysis to the 3D vascular contrasting projection image.

4. The method defined in claim 3, further comprising:
   defining a stage of the mucosa of the digestive tract within the depth range according to the vessel morphological feature.

5. The method defined in claim 3, wherein the vessel morphological feature includes at least one of vessel area density, vessel diameter, and vessel bendiness.

6. The method defined in claim 1, wherein the vessel morphology includes at least one of distribution, shape, bending, branching, merging, meandering, elongation, dilation, uniform, closed loop and opened loop.

7. The method defined in claim 1, wherein an all 3D vascular contrasting projection image of the all of the mucosa of the digestive tract within the depth range is reconstructed by performing the projection process to the all 3D vascular contrasting image.

8. The method defined in claim 7, further comprising:
obtaining the vessel morphological feature of the all of the mucosa of the digestive tract within the depth range by performing a quantitative analysis on the all 3D vascular contrasting projection image.

9. The method defined in claim 1, wherein the part 3D vascular contrasting image of the part of the mucosa of the digestive tract within the depth range is constructed by recombining a part of the plurality of 2D vascular images.

10. The method defined in claim 9, wherein a part 3D vascular contrasting projection image of the part of the mucosa of the digestive tract within the depth range is reconstructed by performing the projection process to the part 3D vascular contrasting image.

11. The method defined in claim 10, further comprising:
obtaining the vessel morphological feature of the part of the mucosa of the digestive tract within the depth range by performing a quantitative analysis on the part 3D vascular contrasting projection image.

12. The method defined in claim 1, wherein the digestive tract is oral cavity, esophagus, stomach or intestines.

13. The method defined in claim 1, wherein the depth range is 0.001 mm to 15 mm.

14. The method defined in claim 1, further comprising:
transmitting a light to the mucosa of the digestive tract within the depth range; and
receiving the reply signals from the mucosa of the digestive tract within the depth range, wherein the reply signals are a plurality of combinations coming from a reflected light of the mucosa at different depth within the depth range and a reference light.

15. The method defined in claim 1, wherein the 3D vascular contrasting projection image is reconstructed by projecting the 3D vascular contrasting image on a plane.

16. A system for detecting and analyzing a mucosa of a digestive tract, the system comprising:
a transmission apparatus transmitting a light into the mucosa of the digestive tract within a depth range;
a probe connected to the transmission apparatus and receiving a reflected light from the mucosa of the digestive tract within the depth range; and
a processor connected to the transmission apparatus and configured to:
detect a plurality of reply signals from the reflected light from the mucosa of the digestive tract within the depth range;
acquire a plurality of 2D vascular images of the mucosa of the digestive tract within the depth range by performing a vascular enhancement on the plurality of reply signals;
construct a 3D vascular contrasting image of at least part of the mucosa of the digestive tract within the depth range by recombining at least part of the plurality of 2D vascular images;
reconstruct a 3D vascular contrasting projection image of the at least part of the mucosa of the digestive tract within the depth range by performing a projection process to the 3D vascular contrasting image, wherein at least one of the 3D vascular contrasting projection image, the 3D vascular contrasting image, and the 2D vascular images shows a vessel morphology of the at least part of the mucosa of the digestive tract within the depth range, wherein an all 3D vascular contrasting image of all of the mucosa of the digestive tract within the depth range is constructed by recombining all of the plurality of 2D vascular images;
segment the all 3D vascular contrasting image to form a part 3D vascular contrasting image;
reconstruct a part 3D vascular contrasting projection image of the part of the mucosa of the digestive tract within the depth range by performing the projection process to the part 3D vascular contrasting image; and
obtain a vessel morphological feature of the part of the mucosa of the digestive tract within the depth range by performing a quantitative analysis on the part 3D vascular contrasting projection image.

17. The system defined by claim 16, the processor is further configured to:
obtain a vessel morphological feature of the at least part of the mucosa of the digestive tract within the depth range by performing a quantitative analysis to the 3D vascular contrasting projection image; and
define a stage of the mucosa of the digestive tract within the depth range according to at least one of the 3D vascular contrasting image, the 3D vascular contrasting projection image, the vessel morphology, and the vessel morphological feature.

* * * * *